(12) United States Patent
McSweeney (10) Patent No.: US 10,186,352 B2
(45) Date of Patent: Jan. 22, 2019

(54) SKIN BUTTON WITH FLAT CABLE

(71) Applicant: HeartWare, Inc., Mounds View, MN (US)

(72) Inventor: Timothy McSweeney, South Miami, FL (US)

(73) Assignee: Medtronic HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 15/446,724

(22) Filed: Mar. 1, 2017

(65) Prior Publication Data

US 2017/0256339 A1 Sep. 7, 2017

Related U.S. Application Data

(60) Provisional application No. 62/302,459, filed on Mar. 2, 2016.

(51) Int. Cl.
| | | |
|---|---|---|
| *H01R 24/76* | (2011.01) | |
| *H01B 17/26* | (2006.01) | |
| *A61M 1/10* | (2006.01) | |
| *H01B 3/00* | (2006.01) | |
| *H01B 3/46* | (2006.01) | |
| *H01B 13/012* | (2006.01) | |
| *H01R 12/77* | (2011.01) | |

(Continued)

(52) U.S. Cl.
CPC ........... *H01B 17/26* (2013.01); *A61M 1/1008* (2014.02); *A61M 1/127* (2013.01); *H01B 3/00* (2013.01); *H01B 3/465* (2013.01); *H01B 13/01254* (2013.01); *H01R 12/778* (2013.01); *H01R 24/76* (2013.01); *H01R 43/005* (2013.01)

(58) Field of Classification Search
CPC .... H01R 2201/12; H01R 24/58; H01R 11/30; H01R 12/778; H01R 13/15; H01R 13/187; H01R 13/193; H01R 13/20; H01R 13/22; H01R 13/5224; H01R 24/76; H01R 43/005; H01R 43/26; H01R 4/4881
See application file for complete search history.

(56) References Cited

U.S. PATENT DOCUMENTS

| | | | |
|---|---|---|---|
| 4,412,721 A | 11/1983 | Saatze | |
| 4,676,891 A | 6/1987 | Braa et al. | |

(Continued)

FOREIGN PATENT DOCUMENTS

| | | |
|---|---|---|
| EP | 0864333 A2 | 9/1998 |
| WO | 2012101267 A1 | 8/2012 |
| WO | 2014001501 A2 | 1/2014 |

OTHER PUBLICATIONS

International Search Report and Written Opinion dated Jun. 1, 2017 for International Application No. PCT/US2017/020215, International Filing Date—Mar. 1, 2017 consisting of 11-pages.

*Primary Examiner* — Truc T Nguyen
(74) *Attorney, Agent, or Firm* — Christopher & Weisberg, P.A.

(57) ABSTRACT

A percutaneous connector assembly including a feedthrough assembly having a body and a plurality of electrically conductive feedthroughs extending through the body from a first end toward a second end thereof. A cable assembly having a plurality of conductors arranged side-by-side within a first plane to form a substantially flat portion thereof is included, each conductor being connected to a corresponding feedthrough of the feedthrough assembly and the flat portion extending from the body.

18 Claims, 7 Drawing Sheets

(51) Int. Cl.
*H01R 43/00* (2006.01)
*A61M 1/12* (2006.01)

(56) References Cited

U.S. PATENT DOCUMENTS

| | | | |
|---|---|---|---|
| 4,769,906 A | | 9/1988 | Purpura et al. |
| 4,911,657 A | * | 3/1990 | Berlin .................. A61B 5/0408 |
| | | | 439/258 |
| 4,973,238 A | | 11/1990 | Kihlken et al. |
| 5,201,903 A | | 4/1993 | Corbett, III et al. |
| 5,743,754 A | * | 4/1998 | Cristich ............. H01R 13/6277 |
| | | | 439/349 |
| 5,782,645 A | | 7/1998 | Stobie et al. |
| 5,904,646 A | | 5/1999 | Jarvik |
| 6,084,181 A | | 7/2000 | Lilienthal, II et al. |
| 6,173,101 B1 | | 1/2001 | Bourghelle et al. |
| 6,717,058 B2 | | 4/2004 | Booth et al. |
| 8,772,636 B2 | | 7/2014 | Yamaguchi et al. |
| 8,956,166 B2 | * | 2/2015 | Ritner .................... H01R 12/79 |
| | | | 439/84 |
| 9,093,801 B2 | * | 7/2015 | Williams ............. H01R 12/716 |
| 2007/0167089 A1 | * | 7/2007 | Gobron ................ H01R 13/025 |
| | | | 439/860 |
| 2010/0256440 A1 | * | 10/2010 | Maher ............... A61M 39/0247 |
| | | | 600/16 |
| 2015/0320991 A1 | * | 11/2015 | Sabin ................ A61M 39/0247 |
| | | | 604/288.01 |
| 2016/0175502 A1 | | 6/2016 | McSweeney et al. |

* cited by examiner

SKIN BUTTON WITH FLAT CABLE

CROSS-REFERENCE TO RELATED APPLICATION

This application is related to and claims priority to U.S. Provisional Patent Application Ser. No. 62/302,459, filed Mar. 2, 2016, entitled SKIN BUTTON WITH FLAT CABLE, the entirety of which is incorporated herein by reference.

STATEMENT REGARDING FEDERALLY SPONSORED RESEARCH OR DEVELOPMENT n/a

TECHNICAL FIELD

The present invention relates to a method and system for a percutaneous connector assembly for a mechanical circulatory support device.

BACKGROUND

Many individuals suffer from severe heart failure which is characterized by frequent hospitalizations, severe physical disability, and significantly shortened life spans. Heart transplantation can be a life-saving procedure and may greatly improve the quality of life of the patient. However, donor hearts are in short supply and patients often do not survive long enough to receive this potentially life-saving procedure.

Several medical devices have been developed as an alternative or a bridge to heart transplantation that may prolong the life and even improve the quality of life of a patient suffering from severe heart failure. One such device is a heart pump, commonly referred to as a mechanical circulatory support device (MCSD), such as a ventricular assist device ("VAD"). VADs are typically implanted within the patient such that an inflow of the pump is connected to a heart's left ventricle and an outflow of the pump is connected to the patient's aorta. During operation the pump may assist the left ventricle, which may be significantly impaired, in distributing oxygenated blood throughout the body.

Most blood pumps utilize an external controller and/or power source, which requires an electrical connection be established across the patient's skin between the internal pump and external controller/power source. This is typically achieved by a percutaneous connector, which is connected to the patient's skin and includes a cable that is routed through the patient's body from the connector to the pump. One such connector is disclosed in U.S. application Ser. No. 14/738,443 filed Jun. 12, 2015, the entirety of which is incorporated by reference herein as if fully set forth herein.

Percutaneous connectors may present several challenges such as infection control and patient comfort. Traditional connectors are placed within an opening in the patient's skin, which can act as a gateway for infectious microorganisms to invade the patient's body and compromise the patient's health, which is likely already in a state of decline. In addition, traditional connectors, which may remain attached to the patient's skin for months or even years, are often bulky and can irritate the skin and other parts of the body disposed below the skin. As such, further improvements are desirable.

SUMMARY

The present invention advantageously provides for a percutaneous connector assembly including a feedthrough assembly having a body and a plurality of electrically conductive feedthroughs extending through the body from a first end toward a second end thereof. A cable assembly having a plurality of conductors arranged side-by-side within a first plane to form a substantially flat portion thereof is included, each conductor being connected to a corresponding feedthrough of the feedthrough assembly and the flat portion extending from the body.

In another aspect of this embodiment, the body includes a side surface extending between and intersecting a first surface of the first end and a second surface of the second end.

In another aspect of this embodiment, the substantially flat portion extends through the side surface of the body.

In another aspect of this embodiment, the body defines an axis, wherein the substantially flat portion extends from the body, and wherein the substantially flat portion defines a width orthogonally arranged relative to the axis of the body, the body extending through the first and second surfaces of the body.

In another aspect of this embodiment, the cable includes a transition portion and a round portion, the transition portion being disposed between the flat portion and the round portion.

In another aspect of this embodiment, the round portion is formed by the plurality of conductors being arranged within more than one plane.

In another aspect of this embodiment, the plurality of conductors includes a first conductor, second conductor, and third conductor, and, within the round portion of the cable assembly, the first conductor is arranged within the first plane, the second conductor is arranged in a second plane, and the third conductor is arranged in a third plane.

In another aspect of this embodiment, the cable assembly includes a jacket forming a plurality of conduits extending along a length thereof and each conductor being disposed within a respective conduit of the jacket.

In another aspect of this embodiment, silicone oil is disposed within each conduit between the jacket and conductors.

In another aspect of this embodiment, each conduit is connected to an adjacent conduit at an interface along the flat portion of the cable assembly, and each conduit is separated from an adjacent conduit at the interface along the transition portion and the round portion.

In another aspect of this embodiment, a jacket of biocompatible material is molded over the jacket along the transition portion and rounded portion of the cable assembly to maintain the separated conduits in a predetermined configuration.

In yet another embodiment, a percutaneous connector assembly includes a feedthrough assembly having a body and a plurality of electrically conductive feedthroughs extending through the body from a first end toward a second end thereof. A skirt connected to the body and extending radially outwardly therefrom is included. A cable assembly having a plurality of conductors arranged side-by-side within a first plane to form a flat portion thereof is included, each conductor being connected to a corresponding feedthrough of the feedthrough assembly and the flat portion extending from the body.

In another aspect of this embodiment, the body includes a side surface extending between and intersecting a first end-surface of the first end and a second end-surface of the second end.

In another aspect of this embodiment, the skirt is attached to the side surface of the body.

In another aspect of this embodiment, the skirt is sintered to the side surface of the body.

In another aspect of this embodiment, the skirt includes an inner portion having first and second surfaces converging toward each other in a radially outward direction.

In another aspect of this embodiment, the second surface extends from an edge of the body defined by the intersection of the side surface and second end-surface of the body.

In another aspect of this embodiment, the skirt includes a skirt edge at a radial extent thereof and a peripheral portion disposed between the inner portion and skirt edge.

In another aspect of this embodiment, the flat portion of the cable assembly extends from the body between the second end-surface and peripheral portion.

In another aspect of this embodiment, the flat portion of the cable assembly extends from the body between the first end-surface and the peripheral portion.

In another aspect of this embodiment, the flat portion of the cable assembly extends from the body and through a portion of the inner portion.

In yet another embodiment, a method of forming a percutaneous connector assembly includes forming a jacket of dielectric material having a plurality of conduits extending along a length thereof, the plurality of conduits being connected to one another at an interface and in a planar arrangement. At least one conductor is positioned within each of the plurality of conduits. Each conduit is separated from an adjacent conduit at the interface along a portion of the jacket and forms a flat portion of connected conduits and a plurality of free lengths of separated conduits. The plurality of free lengths of separated conduits are rearranged and form a round portion of conduits. Each conductor is connected to a corresponding electrically conductive feedthrough of a feedthrough assembly.

In another aspect of this embodiment, forming a jacket of dielectric material and the positioning at least one conductor within each of the plurality of conduits are performed concurrently.

In another aspect of this embodiment, forming a jacket of dielectric material includes laminating the plurality of conductors with the dielectric material.

In another aspect of this embodiment, rearranging the plurality of free lengths of conduits forms a transition portion disposed between the round portion and flat portion.

In another aspect of this embodiment, connecting each conductor to a corresponding electrically conductive feedthrough of a feedthrough assembly includes connecting the conductors extending from the flat portion of conduits to the feedthroughs such that the flat portion extends from a body of the feedthrough assembly.

BRIEF DESCRIPTION OF THE DRAWINGS

The features, aspects, and advantages of the present invention will become better understood with regard to the following description, appended claims, and accompanying drawings in which:

DETAILED DESCRIPTION

As used herein, the terms "about," "generally," and "substantially" are intended to mean that slight deviations from absolute are included within the scope of the term so modified.

Figure 1:
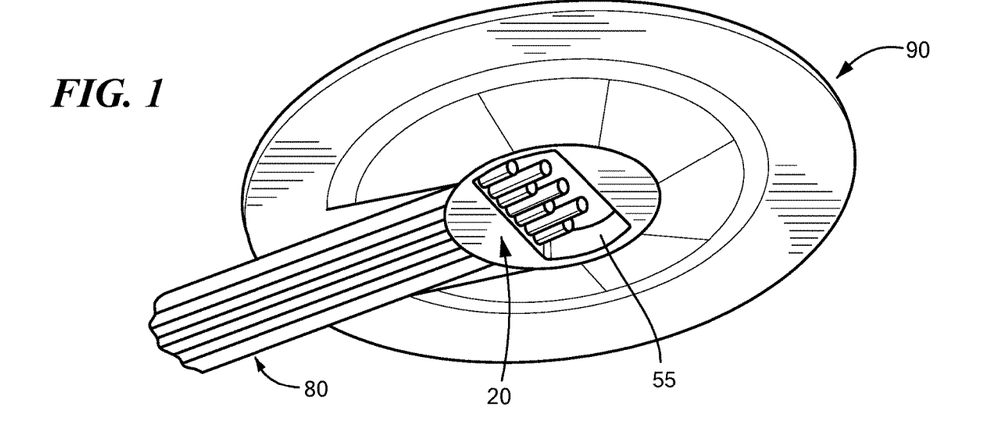
FIG. 1 is a bottom perspective view of a percutaneous connection assembly according an embodiment of the presently disclosed invention including a hermetic feedthrough assembly, cable assembly, and skirt.
Figure 2:
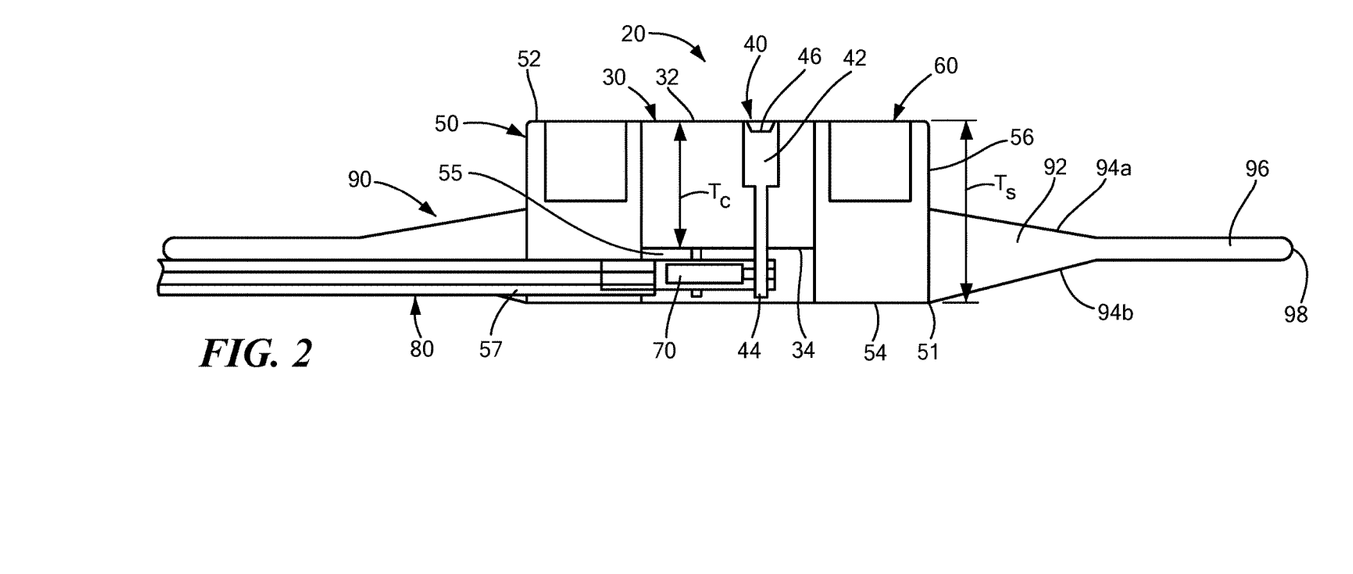
FIG. 2 is a cross-sectional view of the percutaneous connection assembly of FIG. 1 taken along a line bisecting the assembly.

Referring now to the drawing sin which like reference designators refer to like elements, there is shown in FIGS. 1 and 2 a percutaneous connection assembly "10" according to an embodiment of the present invention. Assembly 10 generally includes a hermetic feedthrough assembly 20, cable assembly 80, and skirt 90. Percutaneous connection assembly 10 is configured to have a low profile and provide electrical connection between an internally implantable device and an external controller and/or power supply. One type of internally implantable device contemplated for use with percutaneous assembly 10 is an MCSD disclosed in U.S. Pat. No. 6,688,861, the entirety of which is incorporated by reference herein as if fully set forth herein. An example of an external device that can be used with the percutaneous connection assembly can be found in U.S. Application Publication No. 2010/0241223, the entirety of which is incorporated by reference herein as if fully set forth herein. Other external and internal devices can also be used with percutaneous connection assembly 10.

Figure 3A:
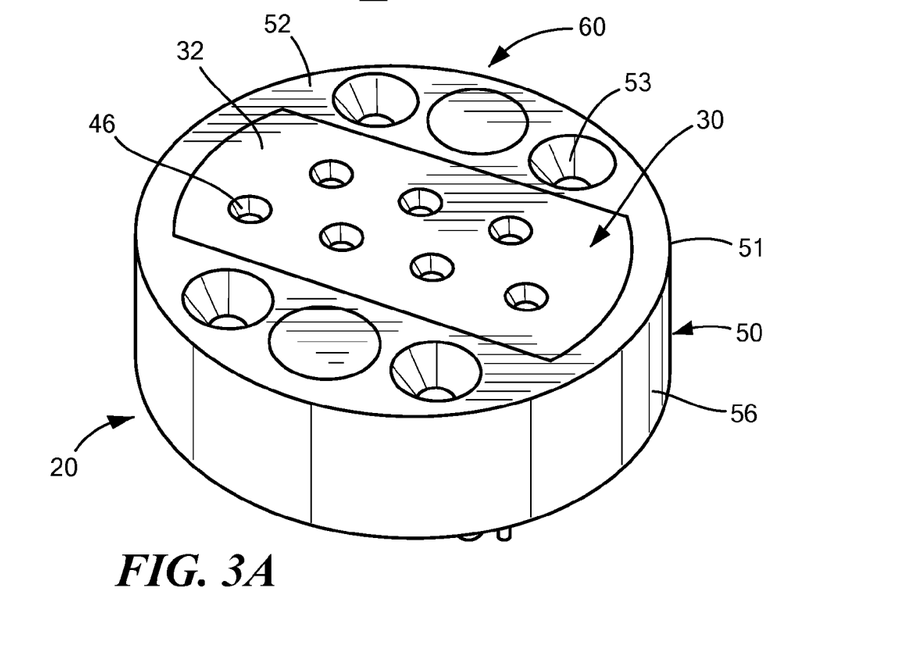
FIG. 3A is a top perspective view of the hermetic feedthrough assembly of the percutaneous connection assembly of FIG. 1 according to an embodiment of the presently disclosed invention and including an core and a shell.
Figure 3B:
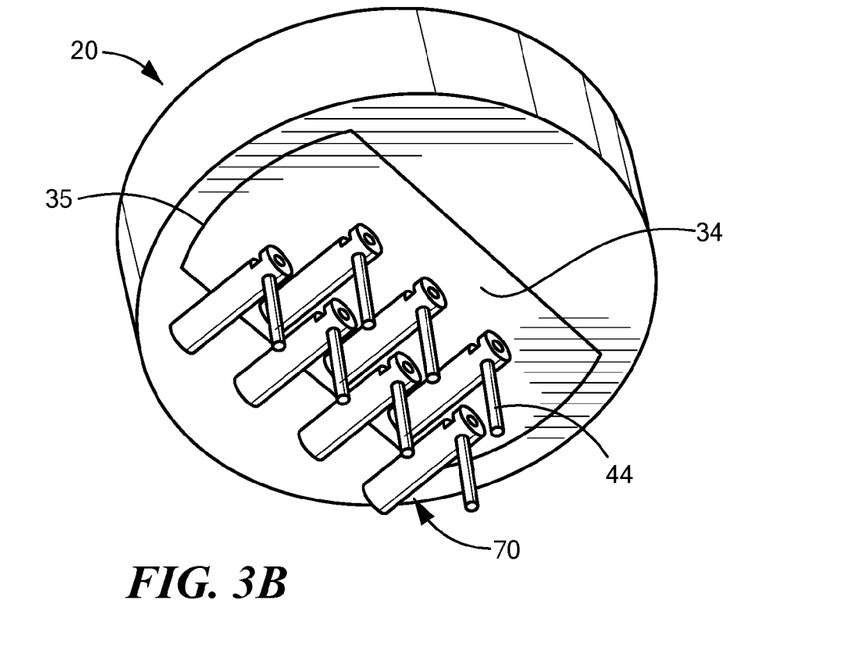
FIG. 3B is a bottom partial cutaway view of the hermetic feedthrough assembly of FIG. 2A with the shell being partially cutaway.

Referring now to FIGS. 3A and 3B, the feedthrough assembly 20 includes a plurality of electrically conductive feedthroughs 40 and a body comprised of a core 30 and a shell 50. Although the body of feedthrough assembly 20 is described throughout as being comprised of both core 30 and a shell 50, it is contemplated that the body may be a monolithic or unitary body, such as a body molded from a dielectric, biocompatible material over an array of feedthroughs 40, for example.

In one configuration, core 30 is made from a glass or ceramic material that is electrically insulating and biocompatible. Core 30 includes a first end-surface 32 at a first end thereof and a second end-surface 34 at a second end thereof. A thickness $T_c$ of core 30 is defined between end surfaces 32 and 34 (best shown in FIG. 2). First and second end-surfaces 32, 34 are intersected by multiple side surfaces, which may be planar and/or convex. In some embodiments, core 30 may be cylindrical and include a single side surface extending about the entire circumference of core 30.

Core 30 also includes a plurality of openings extending through the first and second end-surfaces for receipt of feedthroughs 40. These openings are comprised of first and second sections. As best shown in FIG. 2, the first section intersects with first end-surface 32 and, in one configuration, has a larger diameter or cross-sectional dimension than the second section, which intersects with second end-surface 34. In one configuration, the openings are arranged in side-by-side linear arrays. However, the openings can be arranged in a circular configuration or some other geometric configuration. In the particular embodiment depicted, there are seven openings for receipt of seven feedthroughs 40. However, it is contemplated that there may be more or fewer openings depending on the electrical needs of a downstream implantable device.

Feedthroughs 40 are elongate structures made from electrically conductive material, such as gold, copper, silver, or platinum, for example. Each feedthrough 40 has a first portion 42 and a second portion 44. First portion 42 is generally cylindrical and has a diameter or cross-sectional dimension sized to fit within the first section of one of the core openings. Second portion 44 has a smaller diameter or cross-sectional dimension than that of first portion 42 and is sized to fit within the second section of the core openings.

A concave dome-like surface 46 is located at a free end of first portion 42 of each feedthrough 40. This helps establish a conductive interface with a corresponding convex, conductive surface of a cap assembly connectable to feedthrough assembly 20 for providing power or control signals to an implantable device. Such cap assembly is described in the heretofore referenced '443 application, incorporated by reference herein. Alternatively, dome-like surfaces 46 can be convex for interfacing with corresponding concave surfaces.

In one configuration, shell 50 is made from a biocompatible metal, such as titanium and stainless steel, or a biocompatible polymer, such as polyether ether ketone (PEEK), for example. Shell 50 is generally cylindrical and includes a first end-surface 52 at a first end thereof and a second end-surface 54 at a second end thereof. First and second end-surfaces 52, 54 are substantially planar. However, such end-surfaces 52, 54 can be convexly or concavely curved. A side surface 56 extends between and intersects first and second end-surfaces 52, 54 to form edges 51, which may be rounded to reduce or eliminate their sharpness. One or more of these end and side surfaces 52, 54, 56 may be manufactured to minimize microbial growth or adherence thereto. For example, these surfaces can be manufactured to be extremely smooth, such as by lapping, or to have a micro-topography that is resistant to microbial growth, such as a Sharklet microtopography (Sharklet Technologies, Inc., Aurora, Colo.).

Shell 50 also includes a plurality of hemispherical recesses 53 (FIG. 3A) formed in first end-surface 52 and arranged at predetermined locations for engaging complementary protrusions of a cap assembly to help align the cap assembly with feedthrough assembly 20. In addition, magnets 60 are embedded into first end-surface 52 to facilitate locking engagement with a cap assembly that has complementary magnets.

Further, shell 50 includes a first opening 55 that extends through shell 50 from first end-surface 52 to second end-surface 54 and is sized and shaped to receive core 30 therein. In the depicted embodiment, shell 50 has a thickness $T_S$ defined between first and second end-surfaces 52, 54 that is greater than the thickness $T_I$ of core 30. As such, first opening 55 is generally longer than core 30 is thick. Shell 50 also includes a second or transverse opening 57 which extends through side surface 56 and is in communication with first opening 55. In one configuration, second opening 57 is formed as a shallow slot that is sized to receive cable assembly 80, which is described in further detail below.

In the assembled feedthrough assembly 20, feedthroughs 40 are disposed within corresponding core openings. The differences in diameter between the first and second sections of the core openings creates shoulders for first portions 42 of feedthroughs 40 to rest upon (best shown in FIG. 2). First portions 42 of feedthroughs 40 are positioned within the core openings such that they are flush with first end-surface 32 of core 30. In such embodiment, concave domed-surfaces 46 are recessed beneath first end-surface 32 of core 30, as best shown in FIGS. 2 and 3A. At the opposite end of core 30, second portions 44 of feedthroughs 40 extend from second end-surface 34, as shown in FIG. 2.

Core 30 is disposed within first opening 55 such that first end-surfaces 52 and 32 of shell 50 and core 30, respectively, are aligned or coplanar. Additionally, second end-surface 32 of core 30 terminates before reaching the end of first opening 55, which forms a cavity near the second end of shell 50 (best shown in FIG. 2). Second portions 44 of feedthroughs 40 extend into this cavity. Core 30, feedthroughs 40, and shell 50 are joined together to form a hermetic seal at their corresponding boundaries, which can be performed by metal-ceramic brazing or metal-glass joining as is known in the art. Such hermetic joining helps prevent microorganisms from traveling through feedthrough assembly 20 into a patient when implanted.

Figures 4A, 4B, 4C, 4D, 4E, 4F, 4G:
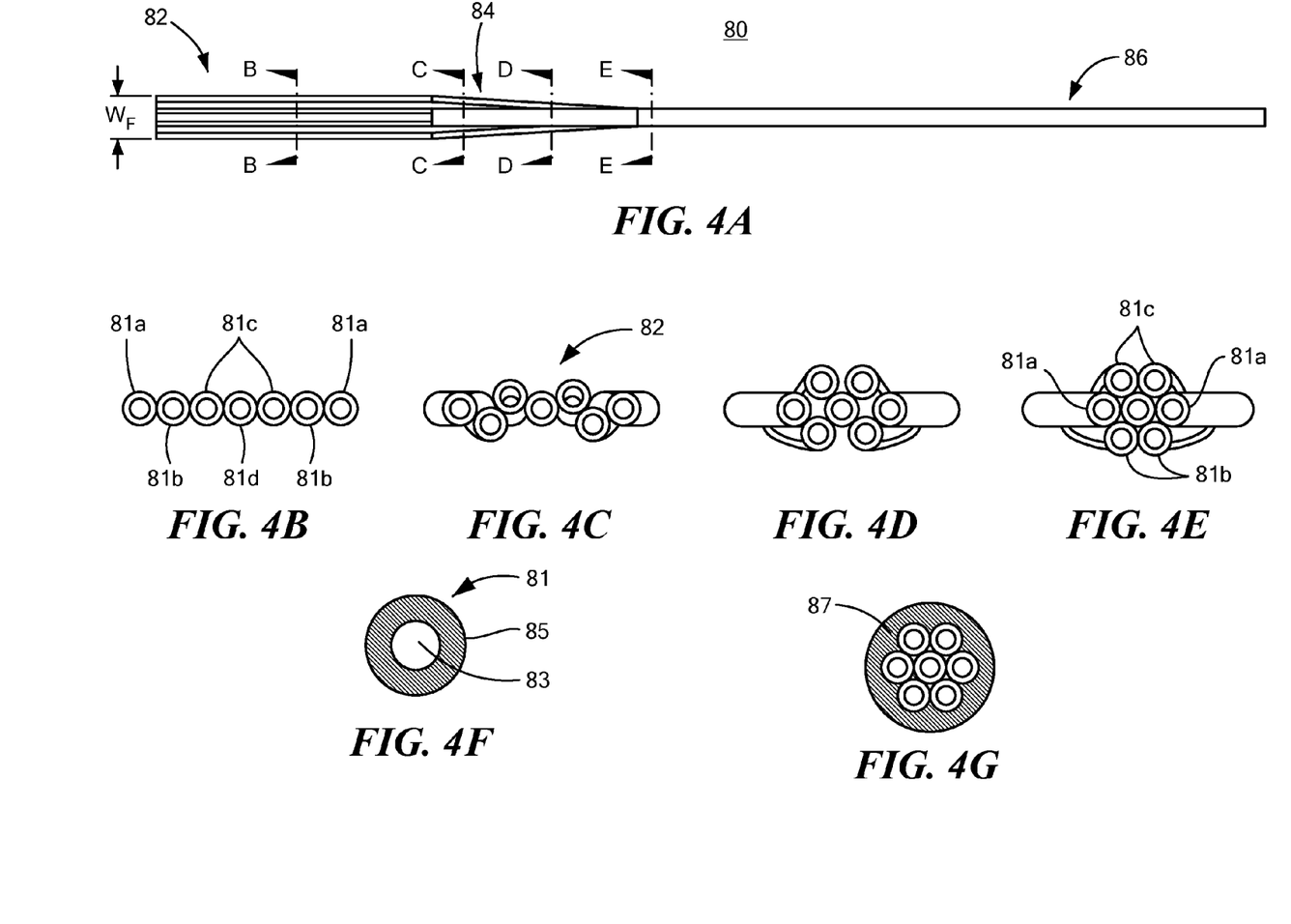
FIG. 4A is a schematic view of a cable assembly of the percutaneous connection assembly of FIG. 1 according to an embodiment of the presently disclosed invention.
FIG. 4B is a cross-sectional view of a flat portion of the cable assembly of FIG. 4A.
FIG. 4C is a cross-sectional view of a transition portion of the cable assembly taken at line C-C of FIG. 4A.
FIG. 4D is a cross-sectional view of the transition portion of the cable assembly taken at line D-D of FIG. 4A.
FIG. 4E is a cross-sectional view of a round portion of the cable assembly taken at line E-E of FIG. 4A.
FIG. 4F is a schematic cross-sectional view of a conductor of the cable assembly of FIG. 4A.
FIG. 4G is a cross-sectional view of the round portion of FIG. 4E surrounded by a jacket.

FIGS. 4A-4F depict cable assembly 80 according to an embodiment of the present disclosure. Cable assembly 80 includes a plurality of insulated conductors 81 arranged into a flat portion 82, transition portion 84, and round portion 86 of the cable assembly. Each conductor 81 is an electrically conductive wire 83 surrounded by insulation 85, which is made from a dielectric, biocompatible material such as polyurethane, silicone, nylon, as best shown in FIG. 4F.

FIG. 4B illustrates a cross-section of flat portion 82 of cable assembly 80. Conductors 81 along flat portion 82 are joined together in a side-by-side configuration such that they are each arranged in a single plane. The insulation 85 covering conductor 81 is joined to the insulation covering the next adjacent conductor 81 at an interface by. This can be achieved, for example, by extruding a plurality of wires 81 with insulation 85, by laminating wires 81 with insulation 85 into the illustrated flat configuration, or by an adhesive disposed at the interfaces between adjacent conductors. In the depicted embodiment, there are seven conductors 81*a-d*. However, it should be understood that more or less conductors 81 may be utilized depending on the electrical needs of the downstream implantable device. In this seven conductor arrangement, a center conductor 81*d* is flanked on each side by three conductors, namely a first flanking conductor 81*a*, second flanking conductor 81*b*, and third flanking conductor 81*c*. As indicated above, each of these conductors 81*a-d* are connected to an adjacent conductor and are arranged in a first plane.

FIGS. 4C and 4D illustrate cross-sections taken at different locations along transition portion 84 of cable assembly 80. Transition portion 84 is that portion of cable assembly 80 along which there is a gradual change in the configuration of conductors 81. Conductors 81 along both transition portion 84 and round portion 86 are separated from each other along their length so that they can be reconfigured into round portion 86. In other words, conductors 81 are disassociated from each other by, for example, separating a conductor 81 from an adjacent conductor 81 at their interface so as to form free-lengths of conductors 81 that are reconfigurable. However, this separation of conductors 81 terminates at flat portion 82 where conductors 81 remain attached to one another.

As shown, within transition portion 84, first flanking conductors 81*a* remain in the first plane while second flanking conductors 81*b* are gradually moved below the first plane into a second plane, and third flanking conductors 81*c* are gradually moved above into a third plane. The movement of second and third flanking conductors 81*b*, 81*c* away from the first plane allows first flanking conductors 81*a* to move inwardly toward center conductor 81*d* (best shown in FIGS. 4C and 4D). At the end of transition portion 84, conductors 81*a-d* are closely arranged into a round configuration, which is illustrated in FIG. 4E. The outline of the flat portion 82 is shown in each of FIGS. 4C-4E for comparison.

Along round portion 86, first flanking conductors 81*a* are located within the first plane along with center conductor 81*d*, the second flanking conductors 81*b* are located in a second plane offset from the first plane, and the third flanking conductors 81*c* are located in a third plane offset from the first and second planes. Such planes, in cross-section, are substantially parallel.

Conductors 81*a-d* desirably are held together to maintain the rounded configuration of round portion 86. For example, a jacket 87 can be applied over round portion 86. Such jacket 87 can also extend over part or all of transition portion 84. Jacket 87 may be made of potting material formed over conductors 81, such as by a two shot process, to allow conductors 81 to be precisely located within the molded material. Alternatively, jacket 87 can be a preformed sleeve of biocompatible material placed about round portion 86. Desirably, the arrangement used to hold the conductors to one another within round portion 86 allows conductors 81 to move slightly relative to one another and relative to jacket 87 to facilitate flexing of round portion 86. To further enhance flexibility of round portion 86, a lubricant (not shown) may be provided on the outer surfaces of insulation layers 85 of the individual conductors. Also, jacket 87 desirably is formed from a relatively soft material to enhance flexibility. If a potting material is used to form jacket 87, the potting material and the insulation of the individual conductors may be selected so that the potting material does not adhere to insulation 85.

In a method of making cable assembly 80, a plurality of wires 83 are laminated from two sides with insulation 85 to form flat portion 82 of cable assembly 80. Alternatively, insulation 85 is molded, extruded or otherwise formed so as to form connected conductors 81*a-d* such that each conductor 81*a-d* is strippable from an adjacent conductor. The resulting assembly includes a length of flat cable comprised of a plurality of conductors 81 arranged side-by-side in a flat configuration.

Each conductor 81*a-d* is stripped or disassociated from one or more adjacent conductors along the length of the flat cable such that the assembly includes a flat portion 82 of connected conductors 81 and free-lengths of separated conductors extending from flat portion 82. The free-lengths of separated conductors 81 are then rearranged to have a round configuration as previously described. However, it should be understood that other arrangements resulting in a round portion 86 are possible and may differ depending on the number of conductors 81 being rearranged. Once conductors 81 are rearranged, a jacket may be applied to the transition and round portions 84, 86 to maintain them in such configuration.

Crimps 70 (FIG. 2), or swages (not shown), can be attached to corresponding conductors 81 at an end of flat portion 82. This may be performed by separating conductors 81 at their interface a length sufficient to allow a crimp 70 to be applied to an end of each conductor 81. Each crimp 70 is a hollow cylindrical structure that is made from conductive material, such as platinum-iridium alloy. Each crimp 70 has a bore extending along the axis of the cylinder and sized to receive the wire 83 of one conductor 81. Each crimp 70 also has a transverse opening which is sized to receive feedthroughs 40. Feedthroughs 40 can be welded or otherwise attached to crimps 70 such that crimps 70 extend orthogonally relative to the feedthroughs and toward second opening 57 of shell 50 (best shown in FIGS. 2 and 3B). Crimps 70 can be used to attach cable assembly 80 to feedthrough assembly 20 without the need for solder.

Skirt 90 is generally disc shaped and includes an inner portion 92 and a peripheral portion 96 (best shown in FIGS. 1 and 2). Inner portion 92 includes first and second surfaces 94*a*, 94*b* that, in one configuration, are conical and converge toward each other in a radially outward direction away from side surface 56 of shell 50. However, in some embodiments surfaces 94*a* and 94*b* can be dome-shaped or some other convex shape rather than conical. Surfaces 94*a* and 94*b* intersect peripheral portion 96, which extends from inner portion 92 to an edge 98 of skirt 90. Edge 98 defines a radial extent of skirt 90. Peripheral portion 96 has a uniform thickness along its radial extent. The conical geometry of inner portion 96 provides rigidity near feedthrough assembly 20 to help prohibit percutaneous assembly 10 from being pulled out from the patient's skin. The geometry of peripheral portion 96 provides flexibility farther from feedthrough assembly 20 to help provide patient comfort.

In the final assemblage of the percutaneous assembly 10, skirt 90 may be formed and connected to side surface 56 of shell 50 by sintering or molding a flowable material, such as a biocompatible polymer or titanium powder, for example, which facilitates a strong connection between skirt 90 and feedthrough assembly 20 as well as closing off potential passageways for microorganisms. In addition, skirt 90 may be formed to have porous or roughened surfaces to facilitate tissue ingrowth. As shown in FIGS. 1 and 2, inner portion 92 is connected to side surface 56 of shell 50 such that second surface 94*b* extends from an edge 51 or very near edge 51 of shell 50. This smoothes edge 51, helping to reduce or eliminate patient discomfort that can be caused by edge 51 rubbing against soft tissue disposed beneath the patient's skin. In addition, the thickness of skirt 90 at the interface between shell 50 and skirt 90 is greater than at edge 98 of the skirt 90. Such thickness at the shell-skirt interface helps reduce shear stress at the interface and prevent disassociation of skirt 90 from feedthrough assembly 20 during use.

Furthermore, transverse opening 57 extends through shell 81 and inner portion 92 of skirt 90 between second end-surface 54 and peripheral portion 96. As mentioned above, core 30 is thinner than sleeve 50. Thus, when core 30 is disposed within opening 55 of sleeve 50, a void is formed between end-surface 34 of core 30 and the second end of sleeve 50. As shown in FIG. 2, this void is in communication with transverse opening 57, and crimps 70 are disposed within the void where they are connected to feedthroughs 40 and extend therefrom in a substantially orthogonal direction. Cable assembly 80 extends through transverse opening 57 into the void where each conductor is connected to a corresponding feedthrough 40 via crimps 70. The void may be filled with a biocompatible potting material to help insulate such connections and to isolate the connections from tissues within the body. This potting material desirably extends to jacket 87 covering the round portion of cable assembly 80 so that the jacket and potting material form a continuous protective covering. Thus, as illustrated in FIG. 2, cable assembly 80 extends from feedthrough assembly 20 between second end-surface 54 of shell 50 and peripheral portion 96 of skirt 90. In other embodiments, transverse opening 57 can be situated such that cable assembly extends from feedthrough assembly 20 between first surface 52 and peripheral portion 96, or through skirt 90 such that cable assembly extends from edge 98.

The portion of cable assembly 80 that connects to and extends away from feedthrough assembly 20 is flat portion 82. Flat portion 82 is arranged so that the width $W_F$ of flat portion 82 is orthogonal to the thickness of feedthrough assembly 20, which is the same as shell-thickness $T_S$. The thickness of feedthrough assembly 20 is large relative to the thickness of flat portion 82 of cable assembly 80. Thus, in the described connection between cable assembly 80 and feedthrough assembly 20, cable assembly 80 occupies a minimal amount of the feedthrough assembly's thickness. This configuration allows for a minimal amount of percutaneous assembly 10 to be disposed beneath the patient's skin and for the overall structure of percutaneous assembly 10 to be compact. In other words, the flatness of cable 80 and its exit location from feedthrough assembly 20 proximate to an end thereof helps minimize the amount of material positioned beneath a patient's skin when implanted.

A method of implanting percutaneous connection assembly 10 in conjunction with an implantable device, such as the MCSD discussed above. The implantable device is electrically connected to percutaneous connection assembly 10 at an end of round portion 86 of cable assembly 80. Such connection may be made during the manufacturing process or intraoperatively. For example, a separable connector (not shown) may be located at the end of round portion 86 remote from feedthrough assembly 20. During the implantation procedure, the separable connector can be coupled to a corresponding connector on the implantable device whenever it is desirable.

A surgical procedure may be performed to gain access to the patient's thoracic cavity or other site where the implantable device is to be placed. The implantable device is connected to the heart or other target organ, as is known in the art. An incision is made in the patient's skin at the location where percutaneous connection device 10 is to be placed as, for example, in the skin covering the abdomen. A hole is formed in the skin adjacent the incision. Feedthrough assembly 20 is placed through the incision, so that skirt 90 is disposed beneath the skin and so that the first end of feedthrough assembly 20 projects out of the skin through the hole. Cable assembly 80 is routed through the patient's body towards the implantable device. For example, round portion 86 of cable assembly 80 may be pulled through a tunnel beneath the skin. The end of round portion 86 remote from feedthrough assembly 20 is connected to the implantable device. This connection may be a direct connection or a connection through one or more intermediate elements. For example, cable assembly 80 may connect with one end of an intermediate cable, and the other end of the intermediate cable may be connected to the implantable device.

As round portion 86 of cable assembly 80 is routed through the patient's body, it flexes to follow the desired routing through anatomical structures. The flexibility in multiple dimensions of round portion 86 is facilitated by its round configuration. Moreover, because the individual conductors are free to move relative to one another within round portion 86, flexibility is enhanced. To further enhance flexibility, a lubricant, such as an oil, can be applied on the insulators of the individual conductors. An external device may include a cap assembly, such as the cap assembly described in the heretofore referenced '443 application. Such cap assembly may include electrical contacts corresponding to feedthroughs 40 and magnets corresponding to magnets 60. The cap assembly, and electrical contacts thereof, may be connected to the portion of the feedthrough assembly 20 protruding from the incision in order to electrically connect the external device to percutaneous connection assembly 10 and consequently to the implantable device. The magnetic attraction of magnets 60 and the magnets of the cap assembly help hold the cap in place.

When placing feedthrough assembly 20 through the incision, feedthrough assembly 50 is pushed through the incision until skirt 90 abuts an internal layer of the skin. Over time, tissue may grow into the porous or rough surfaces of skirt 90 helping to secure feedthrough assembly to the patient's skin. The geometry of inner portion 92 of skirt 90, which is thicker than that of peripheral portion 98, provides sufficient rigidity around the incision to help prevent feedthrough assembly 20 from being pulled through the incision. However, the relatively flexible peripheral portion 96 provides sufficient flexibility of skirt 90 more distant from the incision to minimize patient discomfort. The connection of skirt 90 to feedthrough assembly 20 adjacent the second end thereof of minimizes the amount of feedthrough assembly 20 extending beneath the patient's skin which can help reduce or eliminate irritation that may be caused by edge 51.

Feedthrough assembly 20 is also placed through the incision such that width $W_F$ of flat portion 82 of cable assembly 80 extends from feedthrough assembly 20 in a substantially parallel direction relative to the patient's skin. As flat portion 82 extends from the incision, flat portion 82 curves away from the skin and transitions to round portion 86 which extends toward the heart and implantable device. Although, flat portion 82 is substantially flexible in only one dimension, such multidimensional inflexibility is accounted for by the multidimensional flexibility of round portion 86 of cable assembly 80. This allows the flatness of flat portion 82 help minimize the amount of feedthrough assembly 20 extending beneath the patient's skin while maintaining multidimensional flexibility of cable assembly 80 beneficial in the implantation of the implantable device and percutaneous assembly 10.

Figures 5A, 5B:
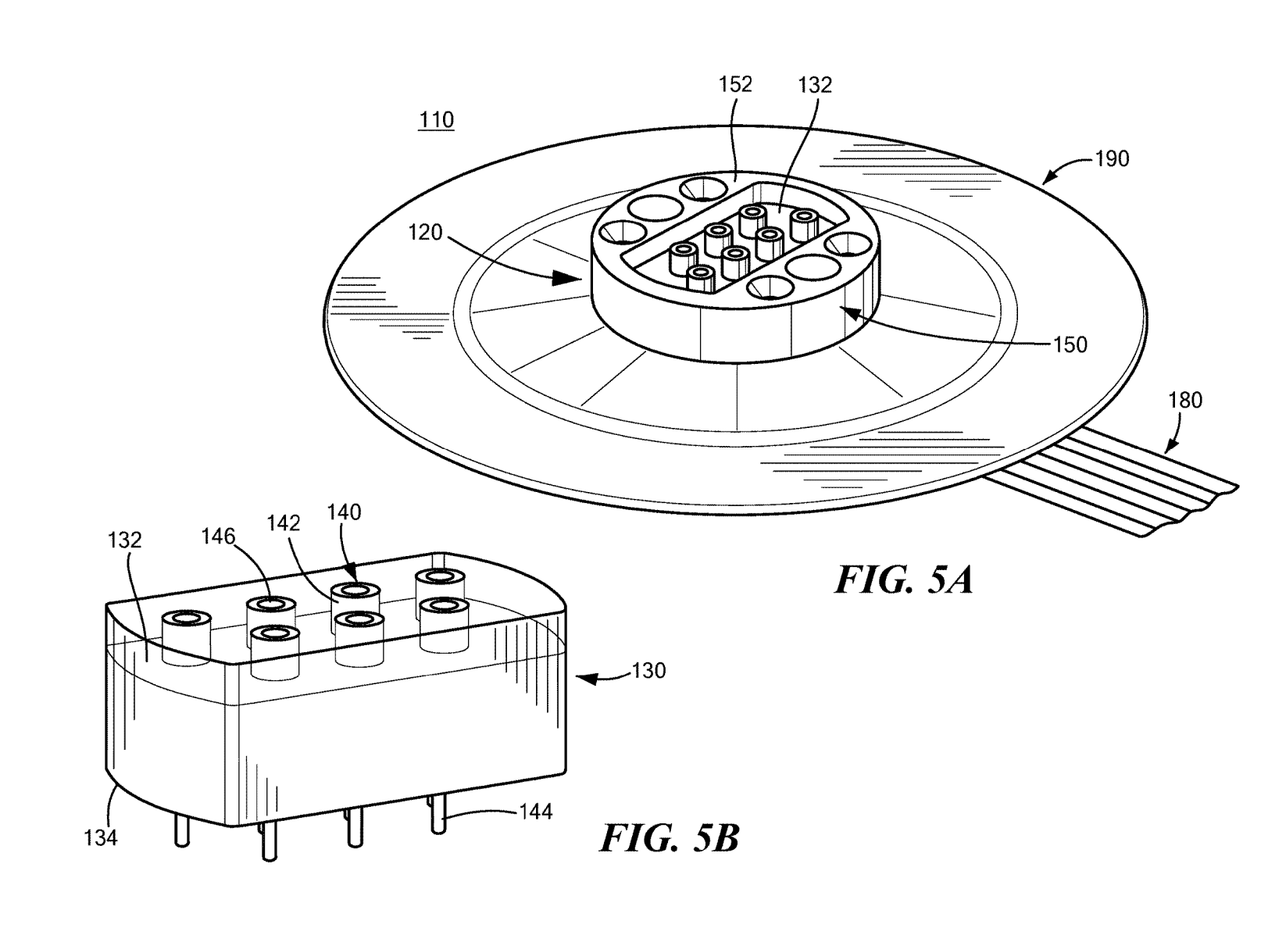
FIG. 5A is a top perspective view of a percutaneous connection assembly according another embodiment of the presently disclosed invention.
FIG. 5B is a perspective view of a core of the hermetic feedthrough assembly of FIG. 5A.

Other alternative embodiments of the aforementioned devices and assemblies are contemplated. FIGS. 5A and 5B depict a percutaneous connector assembly 110 according to another embodiment of the present disclosure. Connector assembly 110 is similar to assembly 10 in that assembly 110 includes a skirt 190 connected to a feedthrough assembly 120 and a flat/round cable assembly 180 extending therefrom. However, assembly 110 differs with regard to core 130. As depicted, core 130 is thinner than core 30 discussed above with reference to FIGS. 1 and 2. The reduced thickness of core 130 is illustrated by the transparent portion in FIG. 5B. When core 130 is inserted into shell 150, first end-surface 132 of core 130 is recessed beneath first end-surface 152 of shell 150. This forms a cavity, which can be filled with potting epoxy or silicone. When assembled, first portions 142 of feedthroughs 140 extend from first end-surface 132 of core 130. The first portions 142 desirably are not fully covered by the potting, so that they remain exposed for contact with mating conductors on a cap. This embodiment can help address potential corrosion issues, such as when gold feedthroughs are brazed to a ceramic core. This embodiment can also help reduce the overall weight of feedthrough assembly 120 or for adaption to a particular plug of an external device.

Figure 6:
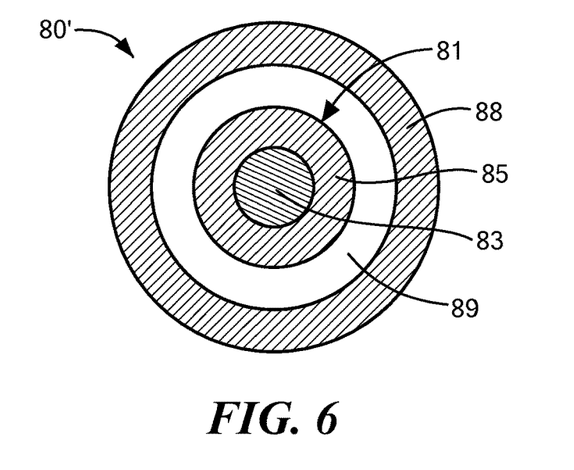
FIG. 6 is a schematic cross-sectional view of a conductor and conduit according to another cable assembly embodiment.

In the embodiment discussed above, the insulation layer 85 of each conductor 81 (FIG. 4F) forms a conduit enclosing only the wire 83 of the conductor. These conduits are connected together to form flat portion 82 and rearranged to form round portion 86. (FIGS. 4A-4G). However, as shown in FIG. 6 each conductor 81, including the insulation layer 81 and wire 83 can be disposed within a lumen 89 of a larger conduit 88. Such conduit 88 can be made from materials similar to insulation 85. Such conduits 88 can be arranged into the flat, transition, and round portions 82, 84, 86 in the same manner described above. Thus, in such a construction 80', each conduit 88 would be connected to an adjacent conduit 88 along flat portion 82 and separated and reconfigured into round portion 86. Silicone oil or another lubricant can be disposed within lumen 89 between conductor 81 and conduit 88 to help reduce friction therebetween.

Figure 7A:
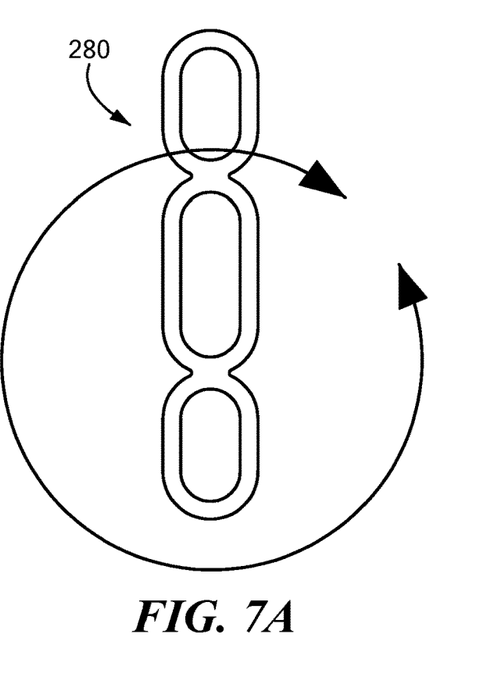
FIG. 7A is a cross-sectional view of a flat portion of a cable assembly according to another embodiment of the presently disclosed invention.
Figure 7B:
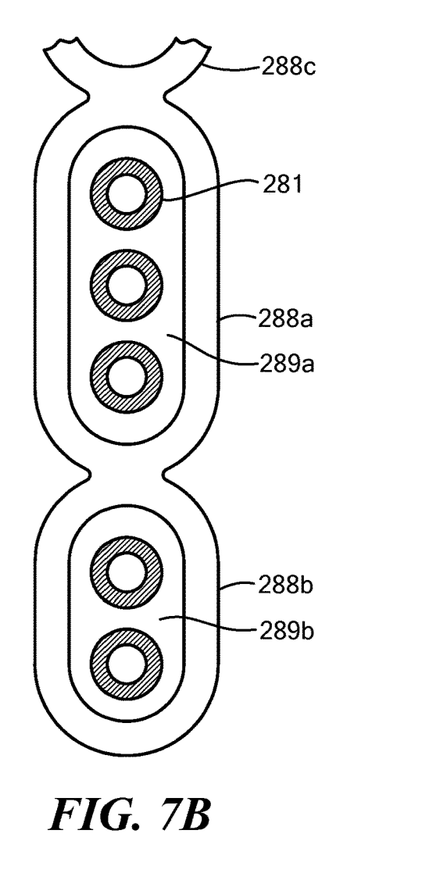
FIG. 7B is a zoomed view of the flat portion of the cable assembly within circle A of FIG. 7A.

FIGS. 7A and 7B depict an alternative embodiment cable assembly 280 which can also be configured to have both round and flat portions. Much like cable assembly construction 80', assembly 280 includes a plurality of conduits 288 attached to one another in a flat configuration. However, cable assembly 280 differs in that one or more of conduits 288 defines a lumen 289 configured to receive multiple conductors 281, therein, rather than a single conductor. For example, in the depicted embodiment, three conduits 288a-c having ovular shaped lumens 289a-c is comprised of a center conduit 288a, and first and second flanking conduits 288b-c. The center conduit 288a, in one configuration, has a wider lumen 289a than adjacent first and second flanking conduits 288b-c. As such, center conduit 288a can receive three conductors 281, and first and second flanking conduits 288b-c can each receive two conductors. In a flat configuration, shown in FIG. 6B, conduits 288a-c are arranged side-by-side in a first plane. In addition, the conductors disposed within each one of the conduits 288a-c are arranged side-by-side in the first plane.

Conduits 288a-c can be separated along a portion of their length and rearranged to form a round portion in addition to a flat portion. This can be achieved by separating conduits 288a-c along a portion of cable assembly 280 and rearranging flanking conduits 288b-c so that center conduit 288a and the conductors 281 disposed therein, remains in the first plane and so that first and second flanking conduits 288b-c, and their respective conductors disposed therein, are disposed in second and third planes, respectively. Owing to the smaller widths of flanking conduits 288b-c, the general profile of this configuration is round, rather than flat.

Although cable assembly 280 is described as having a plurality of conduits each containing one or more conductors therein, cable assembly 280 can be similar to assembly 80 in that it can be constructed such that portions 288a-c are constructed only of wires disposed within insulation. Stated another way, the material forming the wall of conduit 288a may extend between the wires and insulate the wires disposed within conduit 288a from one another.

Although certain exemplary embodiments of flat/round cable assemblies have been described herein, it should be understood that any cable that transitions from a flat to round cable can be utilized in percutaneous connector assemblies 10 and 110 described herein. For example, the cable assemblies are described herein as having a plurality of conductors (or conduits containing such conductors) that are integrally joined along a flat portion of the assembly and separated into individual lengths along a round portion of the assembly. However, in some embodiments a cable assembly can be alternatively configured such that it includes a plurality of individual conductors (i.e., separate from one another) arranged into flat and round portions, which can be bound together to maintain their flat and round configurations. In other embodiments, a cable assembly may include a plurality of conductors (or conduits containing such conductors) integrally joined along their entire lengths into a side-by-side flat cable. Such cable can be arranged into a round portion by rolling or folding the integrally joined conductors and disposing the rolled or folded cable within a round jacket to maintain the rounded configuration. Portions of the conductors not within the round jacket can be unfolded or unrolled into a flat portion. Examples of such cables and other round/flat cables can be found in U.S. Pat. Nos. 4,412,721; 4,973,238; 4,676,891; 6,717,058; 5,201,903; 6,173,101; 4,769,906; 6,084,181 and 8,772,636 all of which are hereby incorporated herein by reference in their entireties.

Figure 8:
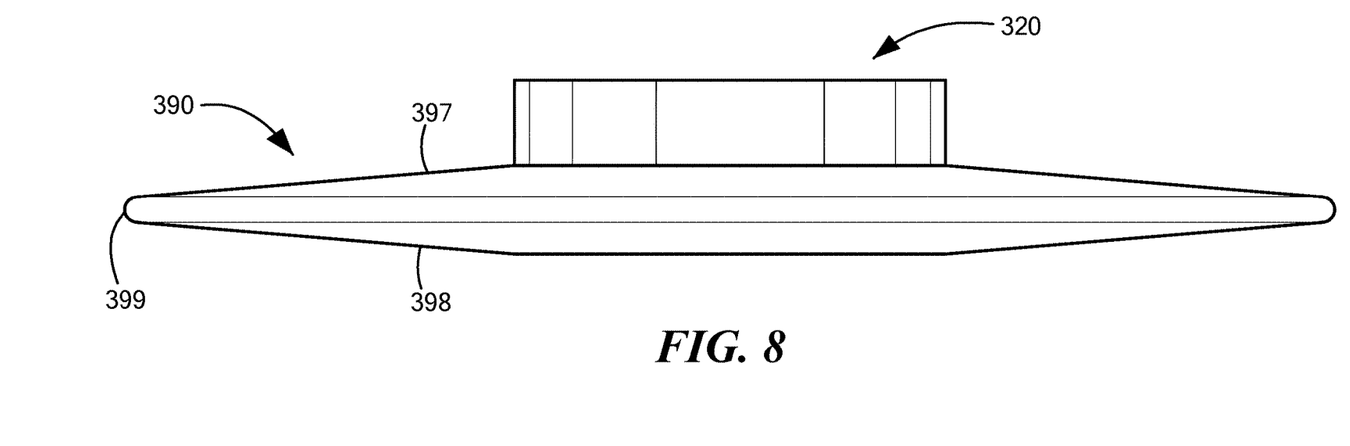
FIG. 8 is a side view of a skirt according to another embodiment of the presently disclosed invention.

FIG. 8 depicts a skirt 390 according another embodiment of the present disclosure. Skirt 390 is similar to skirt 90 in that skirt 390 may be sintered to feedthrough assembly 320. In addition, skirt 390 includes converging surfaces 397 and 398 extending from feedthrough assembly 320 in order to provide rigidity near percutaneous assembly 320 and flexibility far from percutaneous assembly 320. However, unlike skirt 90, skirt 390 does not include a peripheral portion of uniform thickness. Rather, surfaces 397 and 398 converge to an edge 399 at a radial extent of skirt 390. Such embodiment has a different rigidity/flexibility profile than skirt 90 and may be utilized when such characteristics are desired.

Figure 9:
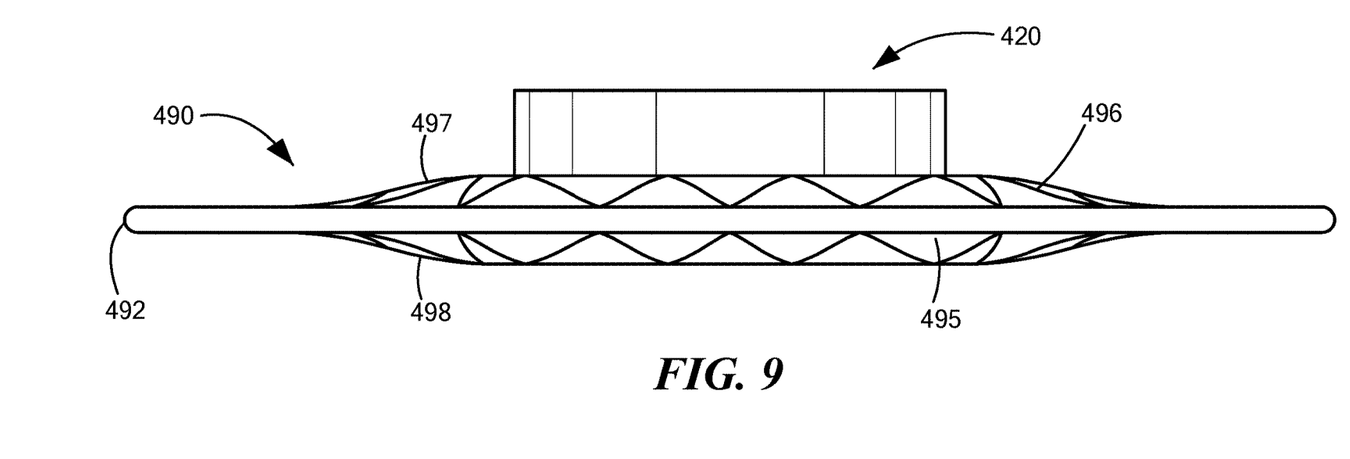
FIG. 9 is a side view of a skirt according to a further embodiment of the presently disclosed invention.

FIG. 9 depicts a skirt 490 according to a further embodiment of the present disclosure. Skirt 490 is similar to skirt 90 in that skirt 490 may be sintered to feedthrough assembly 420. In addition, skirt 490 includes converging surfaces 497 and 498 extending from feedthrough assembly 420 and converging to a peripheral portion 492. However, unlike skirt 90, surfaces 497 and 498 are comprised of plurality of polygonal surfaces 495 interfacing one another to form a generally conical taper from feedthrough assembly 420 to peripheral portion 492. Such embodiment has a different rigidity/flexibility profile than skirt 90 and may be utilized when such characteristics are desired.

Figure 10A:
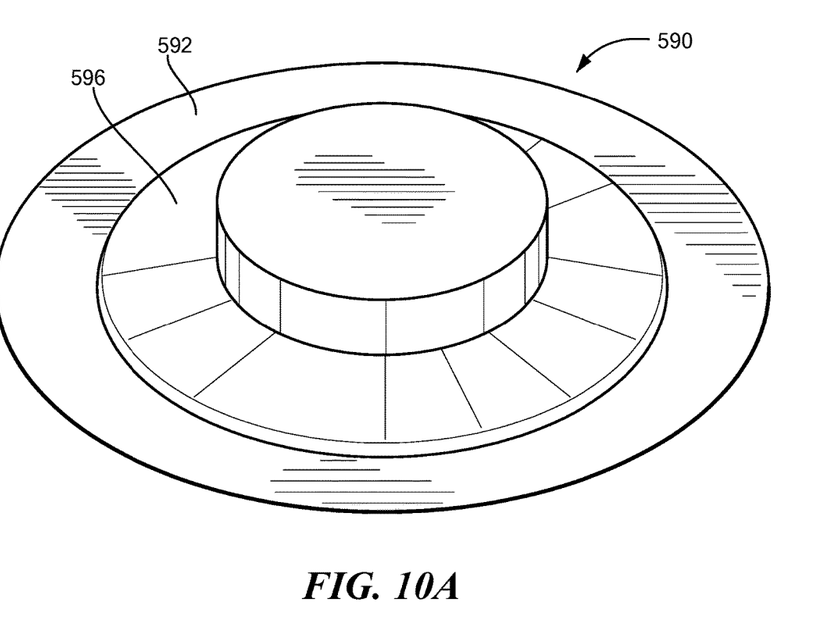
FIG. 10A is a perspective view of a skirt according to yet another embodiment of the presently disclosed invention.
Figure 10B:
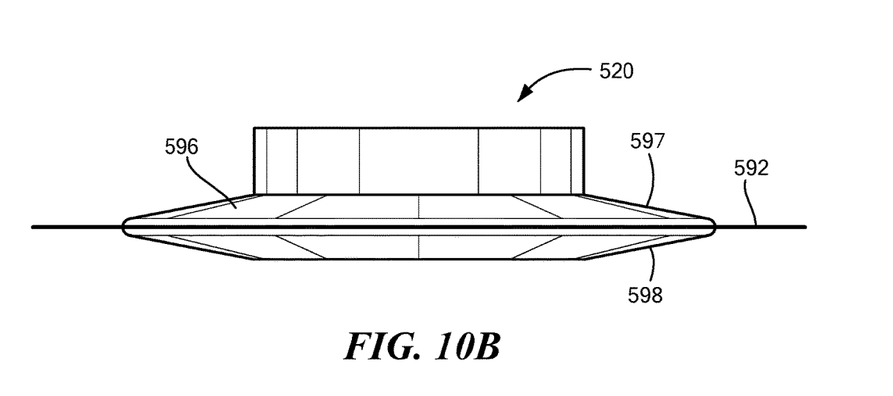
FIG. 10B is a side view of the skirt of FIG. 10A.

FIGS. 10A and 10B depict a skirt 590 according to yet another embodiment of the present disclosure. Skirt 590 is similar to skirt 90 in that skirt 590 may be sintered to feedthrough assembly 520. In addition, skirt 590 includes tapered surfaces 597 and 598 extending from feedthrough assembly 520 and converging to a peripheral portion 592. However, unlike skirt 90, peripheral portion 592 is a mesh disc integrated into the structure of inner portion 596 by sintering inner portion 596 to mesh disc 592. Such embodiment has a different rigidity/flexibility profile than skirt 90 and may be utilized when such characteristics are desired.

Although connector assemblies 10 and 110 have been described above in relation to an MCSD, it should be understood that the herein described connector assemblies may be utilized in conjunction with any implantable device, such as an implantable renal assist device (IRAD), for example.

In addition, it should be understood that the described magnetic interface between feedthrough assembly 20 and a cap assembly of an external device are not essential. Feedthrough assembly 20 can be mechanically connected to a cap or to another component of an external device using other means, such as a threaded connection or tapered male-female connection.

Furthermore, it should be understood that feedthroughs 40 may have alternative configurations rather than recess 46 to facilitate interconnection with an external device. For example, feedthroughs 40 may extend from feedthrough assembly 20 as an array of pins which are receivable in conductive openings of a cap assembly.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention. The following paragraphs further describe certain aspects of the invention.

What is claimed is:

1. A percutaneous connector assembly comprising:
a feedthrough assembly having a body and a plurality of electrically conductive feedthroughs extending through the body from a first end toward a second end thereof; and
a cable assembly having a plurality of conductors arranged side-by-side within a first plane to form a substantially flat portion thereof, each conductor being connected to a corresponding feedthrough of the feedthrough assembly and the flat portion extending from the body, wherein the cable includes a transition portion and a round portion, the transition portion being disposed between the flat portion and the round portion.

2. The assembly of claim 1, wherein the body includes a side surface extending between and intersecting a first surface of the first end and a second surface of the second end.

3. The assembly of claim 2, wherein the substantially flat portion extends through the side surface of the body.

4. The assembly of claim 2, wherein the body defines an axis, wherein the substantially flat portion extends from the body, and wherein the substantially flat portion defines a width orthogonally arranged relative to the axis of the body, the body extending through the first and second surfaces of the body.

5. The assembly of claim 1, wherein the round portion is formed by the plurality of conductors being arranged within more than one plane.

6. The assembly of claim 1, wherein the plurality of conductors includes a first conductor, second conductor, and third conductor, and, within the round portion of the cable assembly, the first conductor is arranged within the first plane, the second conductor is arranged in a second plane, and the third conductor is arranged in a third plane.

7. The assembly of claim 1, wherein the cable assembly includes a jacket forming a plurality of conduits extending along a length thereof and each conductor being disposed within a respective conduit of the jacket.

8. The assembly of claim 7, wherein silicone oil is disposed within each conduit between the jacket and conductors.

9. The assembly of claim 7, wherein each conduit is connected to an adjacent conduit at an interface along the flat portion of the cable assembly, and each conduit is separated from an adjacent conduit at the interface along the transition portion and the round portion.

10. The assembly of claim 9, wherein a jacket of biocompatible material is molded over the jacket along the transition portion and rounded portion of the cable assembly to maintain the separated conduits in a predetermined configuration.

11. A percutaneous connector assembly comprising:
a feedthrough assembly having a body and a plurality of electrically conductive feedthroughs extending through the body from a first end toward a second end thereof, the first end including a first end-surface and the second end including a second end-surface, and the body including a side surface extending between and intersecting the first end-surface of the first end and the second end-surface of the second end;
a skirt connected to the body and extending radially outwardly therefrom, the skirt including an inner portion having first and second surfaces converging toward each other in a radially outward direction; and
a cable assembly having a plurality of conductors arranged side-by-side within a first plane to form a flat portion thereof, each conductor being connected to a corresponding feedthrough of the feedthrough assembly and the flat portion extending from the body.

12. The assembly of claim 11, wherein the skirt is attached to the side surface of the body.

13. The assembly of claim 11, wherein the skirt is sintered to the side surface of the body.

14. The assembly of claim 11, wherein the second surface extends from an edge of the body defined by the intersection of the side surface and second end-surface of the body.

15. The assembly of claim 11, wherein the skirt includes a skirt edge at a radial extent thereof and a peripheral portion disposed between the inner portion and skirt edge.

16. The assembly of claim 15, wherein the flat portion of the cable assembly extends from the body between the second end-surface and peripheral portion.

17. The assembly of claim 15, wherein the flat portion of the cable assembly extends from the body between the first end-surface and the peripheral portion.

18. The assembly of claim 15, wherein the flat portion of the cable assembly extends from the body and through a portion of the inner portion.

* * * * *